(12) United States Patent
Park et al.

(10) Patent No.: US 8,465,768 B2
(45) Date of Patent: Jun. 18, 2013

(54) PHARMACEUTICAL COMPOSITIONS FOR RELEASE CONTROL OF METHYLPHENIDATE

(75) Inventors: Sang Yeob Park, Daejeon (KR); Hojin Chung, Daejeon (KR); Chaul Min Pai, Daejeon (KR)

(73) Assignee: Samyang Biopharmaceuticals Corporation, Seoul (KR)

( * ) Notice: Subject to any disclaimer, the term of this patent is extended or adjusted under 35 U.S.C. 154(b) by 0 days.

(21) Appl. No.: 13/126,855

(22) PCT Filed: Nov. 6, 2009

(86) PCT No.: PCT/KR2009/006510
§ 371 (c)(1),
(2), (4) Date: Apr. 29, 2011

(87) PCT Pub. No.: WO2010/053306
PCT Pub. Date: May 14, 2010

(65) Prior Publication Data
US 2011/0223247 A1   Sep. 15, 2011

(30) Foreign Application Priority Data
Nov. 7, 2008   (KR) .................. 10-2008-0110351

(51) Int. Cl.
*A61K 9/58* (2006.01)

(52) U.S. Cl.
USPC ........................................................ 424/462

(58) Field of Classification Search
None
See application file for complete search history.

(56) References Cited

U.S. PATENT DOCUMENTS

| | | | | |
|---|---|---|---|---|
| 5,837,284 A * | 11/1998 | Mehta et al. | ............... | 424/459 |
| 6,228,398 B1 * | 5/2001 | Devane et al. | ............... | 424/484 |
| 6,344,215 B1 * | 2/2002 | Bettman et al. | ............... | 424/459 |
| 6,475,493 B1 * | 11/2002 | Mulye | ............... | 424/400 |
| 6,555,127 B2 * | 4/2003 | Steiner | ............... | 424/439 |
| 6,627,223 B2 * | 9/2003 | Percel et al. | ............... | 424/471 |
| 6,635,680 B2 * | 10/2003 | Mulye | ............... | 424/471 |
| 6,673,367 B1 * | 1/2004 | Goldenheim et al. | ............... | 424/464 |
| 6,730,325 B2 * | 5/2004 | Devane et al. | ............... | 424/489 |
| 6,793,936 B2 * | 9/2004 | Devane et al. | ............... | 424/484 |
| 6,902,742 B2 * | 6/2005 | Devane et al. | ............... | 424/484 |
| 7,048,945 B2 * | 5/2006 | Percel et al. | ............... | 424/471 |
| 7,083,808 B2 * | 8/2006 | Goldenheim et al. | ............... | 424/490 |
| 2001/0046472 A1 * | 11/2001 | Steiner | ............... | 424/44 |
| 2001/0046964 A1 * | 11/2001 | Percel et al. | ............... | 514/29 |
| 2002/0054907 A1 * | 5/2002 | Devane et al. | ............... | 424/469 |
| 2003/0129237 A1 * | 7/2003 | Devane et al. | ............... | 424/470 |
| 2003/0170304 A1 * | 9/2003 | Devane et al. | ............... | 424/469 |
| 2004/0197405 A1 * | 10/2004 | Devane et al. | ............... | 424/469 |
| 2004/0234608 A1 * | 11/2004 | Fleshner-Barak et al. | ..... | 424/488 |
| 2005/0118268 A1 * | 6/2005 | Percel et al. | ............... | 424/471 |
| 2006/0240105 A1 * | 10/2006 | Devane et al. | ............... | 424/470 |
| 2008/0260819 A1 * | 10/2008 | Fleming et al. | ............... | 424/458 |
| 2009/0123515 A1 * | 5/2009 | Taylor et al. | ............... | 424/423 |
| 2010/0278912 A1 * | 11/2010 | Fleshner-Barak et al. | ..... | 424/465 |

FOREIGN PATENT DOCUMENTS

| | | |
|---|---|---|
| KR | 10-0540035 | 12/2005 |
| KR | 10-2008-0026754 | 9/2006 |
| NZ | 511442 | 2/2003 |
| NZ | 508567 | 2/2004 |
| WO | WO 02094227 A1 * | 11/2002 |
| WO | WO 2007/093642 A2 | 8/2007 |

OTHER PUBLICATIONS

Anal, A.K., "Time-controlled pulsatile delivery systems for bioactive compounds," *Recent Patent on Drug Delivery & Formulation* (2007) 1: 73-79.
International Search Report for corresponding International Application No. PCT/KR2009/006510 mailed Jun. 28, 2010.
Form PCT/ISA/237 for corresponding International Application No. PCT/KR2009/006510.
Examination Report for New Zealand Patent Application No. 592665, Nov. 24, 2011.

* cited by examiner

*Primary Examiner* — Robert A Wax
*Assistant Examiner* — Olga V Tcherkasskaya
(74) *Attorney, Agent, or Firm* — Merchant & Gould P.C.

(57) ABSTRACT

Disclosed is a pharmaceutical composition for release control comprising a plurality of particles for release control. The plurality of particles for release control comprise a core material containing methylphenidate and a polymer coating layer for release control formed on the core material. The plurality of particles for release control are divided into two or more groups based on the average thickness of the polymer coating layer for release control. The particle groups are identical in terms of the composition of the polymer in the polymer coating layer, but are different in terms of the average thickness of the coated layer. The pharmaceutical composition for release control according to the present invention may control the release pattern of methylphenidate contained in the core material as desired, and can be used as an oral formulation in a variety of forms such as orally disintegrating tablets, etc.

17 Claims, No Drawings

PHARMACEUTICAL COMPOSITIONS FOR RELEASE CONTROL OF METHYLPHENIDATE

This application is a National Stage Application of PCT/KR2009/006510, filed 6 Nov. 2009, which claims benefit of Serial No. 10-2008-0110351, filed 7 Nov. 2008 in South Korea and which applications are incorporated herein by reference. To the extent appropriate, a claim of priority is made to each of the above disclosed applications.

TECHNICAL FIELD

This disclosure relates to pharmaceutical compositions for release control of methylphenidate.

BACKGROUND ART

Release controlled formulation refers to a drug delivery system used to release a biologically active ingredient such as a drug over in a controlled manner over a long period of time, e.g. 6 to 24 hours, such as in a sustained manner or in a pulsed manner. The release controlled formulation is advantageous that it can be taken less frequently and it keeps steadier levels of the drug in the bloodstream. Furthermore, it can exhibit a desired blood level pattern through a pulsed-type release at specific times. As such, the release controlled formulation can optimize the blood level of the drug as desired, maximize its efficacy, and reduce adverse reactions caused by instant release of the drug. In addition, it can improve patient convenience by controlling drug administration intervals.

Various drug delivery systems for release control have been developed and put into use, including Alza's Osmotic Release Oral Systems (OROS®). However, a formulation based on a single system often results in breakdown of the overall system due to occurrence or deficiency of specific factors or components, which may cause severe adverse effects through instant drug release.

Methylphenidate is a psychostimulant drug acting on the sympathetic nerves, mainly the central nervous system. It is commonly used to treat attention-deficit hyperactivity disorder (ADHD), most commonly diagnosed in children of 6 years or older and juveniles. Usually, it is taken twice a day (in the morning and before lunch). But, sustained-release formulations that can be taken once a day are preferred since the patient frequently forgets to take the medicine at the lunch hour or does not want to be known to have the disorder.

Some existing sustained-release techniques employ a multiparticulate modified release system including a combination of immediate-release particles and modified-release particles of methylphenidate. The immediate-release particles are formed without a polymer coating on the drug layer, so that the drug is released immediately. However, since the bitter taste of the drug is not masked due to the absence of the polymer coating, they are inapplicable to the formulations that are disintegrated in the mouth, such as orally disintegrating tablet, chewable tablet, etc.

Accordingly, there is a need of a composition for release control that can stably control the release pattern of methylphenidate and mask the bitter taste of methylphenidate for a predetermined time upon exposure to the oral environment.

DISCLOSURE

Technical Problem

This disclosure is directed to providing a composition for release control capable of controlling the release pattern of methylphenidate.

The disclosure is also directed to providing an oral formulation for release control of methylphenidate.

The disclosure is also directed to providing an orally disintegrating formulation for release control of methylphenidate.

Technical Solution

In one general aspect, there is provided a pharmaceutical composition for release control including a plurality of particles for release control, the plurality of particles for release control comprise a core material containing methylphenidate and a polymer coating layer for release control formed on the core material, wherein the plurality of particles for release control are identical in terms of the composition of the polymer in the polymer coating layer, but are divided into two or more groups based on the average thickness of the polymer coating layer for release control.

ADVANTAGEOUS EFFECTS

The pharmaceutical composition for release control according to the present disclosure allows the control of the release pattern of methylphenidate included in the core material as desired and can mask the bitter taste of methylphenidate for a predetermined time upon exposure to the oral environment. Furthermore, the composition is applicable to various types of oral formulations, particularly to orally disintegrating tablets.

MODE FOR INVENTION

A pharmaceutical composition for release control of methylphenidate according to an embodiment of the present disclosure comprises a plurality of particles for release control comprising a core material containing methylphenidate and a polymer coating layer for release control formed on the core material, wherein the plurality of particles for release control are identical in terms of the composition of the polymer in the polymer coating layer, but are divided into two or more groups based on the average thickness of the polymer coating layer for release control.

In another embodiment, the polymer coating layer for release control may comprise a single layer or two or more layers, if necessary. By forming the coating layer as a single layer or two or more layers, the drug release pattern may be controlled more variously. When the polymer coating layer comprises two or more layers, each layer may be identical or different in terms of the composition of the polymer. For example, the polymer coating layer for release control may be formed of 2 to 5 layers, and each layer may be identical or different in terms of the composition of the polymer.

The pharmaceutical composition for release control according to the present disclosure allows the control of the release pattern of the drug component included in the core material as desired, and is capable of masking the bitter taste of methylphenidate for a predetermined time, specifically for 1 minute or longer, specifically for 3 minutes or longer, for example, upon exposure to the oral environment.

The methylphenidate may be methylphenidate in free base form, a pharmaceutically acceptable salt of methylphenidate, an isomer of methylphenidate, or a mixture thereof. In an embodiment, the methylphenidate may be methylphenidate hydrochloride.

The "particle group" as used herein collectively refers to an assembly, mixture or group of particles of the coating layer having a same average thickness. The particles of each group may be assemble themselves or may be randomly mixed with the particles of other particle group(s).

The "release control" as used herein refers to the state in which the release pattern of the included biologically active ingredient is controlled as desired, and includes controlled release, sustained release, extended release, pulsed release or combinations thereof.

In an embodiment, the particles of each particle group for release control comprise a core material and a polymer coating layer formed on the core material. The core material comprises methylphenidate. The polymer coating layer of each particle group is identical in terms of the composition of the polymer, but is different in terms of the average thickness thereof. Accordingly, since the release pattern of methylphenidate included in the core material varies depending on the kind, composition and coating thickness of the polymer coating layer, a desired release pattern may be achieved from combination of the particle groups.

In an embodiment, the particles for release control may further comprise one or more coating(s) selected from a sub-coating inside the polymer coating layer and an over-coating outside the polymer coating layer. The sub-coating or over-coating serves to confer or improve various supplementary purposes, such as stabilization or protection of the formulation, coloring, masking of bitter taste, etc., with little or no effect on the release control of the drug.

Core Material Comprising Methylphenidate

In an embodiment, the core material may be methylphenidate or methylphenidate mixed with an inert material. More specifically, the core material may be methylphenidate as it is, methylphenidate coated with a biologically inert material on the surface, methylphenidate incorporated in a porous inert material, or methylphenidate granulated or particulated with an inert material.

In an embodiment, the core material may be prepared using a coater, flow coater, fluidized bed processor, flow granulator, granulator, mixer, or the like. The shape, size and size deviation of the core material are not particularly limited. However, in an embodiment, the core material may have a spherical or nearly spherical shape for uniform coating.

In an embodiment, the core material may have a diameter in the range from 10 to 3000 μm, specifically from 50 to 1500 μm, more specifically from 80 to 1000 μm. In another embodiment, particles having a diameter of 80 to 500 μm may be used when preparing an orally disintegrating tablet or a chewable tablet in order to minimize foreign body sensation in the mouth, but without being particularly limited thereto.

The diameter of the core material may be determined using a particle size analyzer, a microscope or an image analyzer. The deviation of the diameter of the core material may be indicated by the standard deviation of the particle diameter. The diameter deviation indicates the degree of variation from the average particle diameter. The smaller the diameter deviation is, a more uniform coating thickness may be obtained. With a more uniform coating thickness, it is easier to obtain reproducible results since the active ingredient of the drug is released uniformly. In an embodiment, the size deviation of the core material may be from 1 to 200 μm, specifically from 1 to 100 μm, more specifically from 1 to 50 μm.

When methylphenidate satisfies the above-described requirement of the core material as it is, the biologically inert material may not be used. However, when the drug is in fine powder form, has various shapes or has a large size deviation of the drug powder, it may not be suitable as a core material for preparing the particles for release control. In this case, the drug may be prepared into spherical or nearly spherical shape or into a size adequate for coating alone or in combination with an inert material, for example, using the GPCG-1 rotor system, by wet or dry extrusion or spheronization, by granulation, or the like.

In an embodiment according to the present disclosure, the core material may be prepared by incorporating methylphenidate into a spherical or nearly spherical porous material. For example, methylphenidate may be incorporated into an ion-exchange resin, silica (e.g., Rhodia Silica Korea's Zeosil® or Tixosil®) or other porous excipients.

In another embodiment, the core material may be prepared by coating methylphenidate on a spherical or nearly spherical inert seed. For example, methylphenidate may be coated on sugar sphere such as nonpareil sugar, which is an inert sugar processed to spheres of regular size, spherical microcrystalline cellulose such as Celphere™ (Asahi Kasei), or the like. When preparing the core material in this way, methylphenidate may be dissolved in water, an organic solvent or a solvent mixture thereof and then coated by spraying.

The spherical seed may have a diameter of 10 to 3000 μm, specifically 50 to 1500 μm, more specifically 80 to 1000 μm. In another embodiment, when preparing an orally disintegrating tablet or a chewable tablet, particles having a diameter of 80 to 500 μm may be used in order to minimize foreign body sensation in the mouth, but without being particularly limited thereto.

Methylphenidate may be included in the core material in an amount of 20-100 wt % based on the weight of the core material. Specifically, in case the core material is prepared by coating methylphenidate on a seed, the amount of the drug may be 20-80 w % based on the weight of the core material, but without being particularly limited thereto.

When preparing the core material, a variety of biologically inert ingredients may be used for various supplementary purposes, such as coating efficiency, drug stability, appearance, color, protection, maintenance, binding, performance improvement, preparation process improvement, supplementary release control, or the like. The biologically inert ingredient may include a sugar, a sugar alcohol, a polymer material, a colorant, an aromatic, a sweetener, a surfactant, a lubricant, a stabilizer, an antioxidant, a foaming agent, paraffin, wax, a plasticizer, or the like. The selection and usage of the biologically inert material and incorporation thereof into the core material may be easily accomplished by those skilled in the art and may be modified variously. For instance, the biologically inert material may be mixed with methylphenidate when preparing the core material.

Among the biologically inert ingredients, the polymer material may have a supplementary effect on the release of methylphenidate. Otherwise, it may have little or insignificant effect on the release of methylphenidate.

The supplementary effect on the release of methylphenidate means that, although the polymer coating layer for release control mainly controls the release, the polymer material included in the core material also affects supplementarily the release of the drug. In this case, when an in vitro release test is performed using a core material comprising the polymer material as well as methylphenidate, a different release pattern is attained from that of the core material comprising methylphenidate only. Such polymer material is added to supplement the release control in case where effective release control is difficult with the core material comprising methylphenidate only or it is desired to attain a comparable effect while reducing the average thickness of the polymer coating layer for release control. Specifically, the polymer material may be a water-insoluble polymer, an enteric polymer, etc.

Also, the little or insignificant effect on the release of methylphenidate means that the polymer material included in the core material comprising methylphenidate has little effect on the release of the drug. In this case, when an in vitro release test is performed using a core material comprising the polymer material as well as methylphenidate, the release pattern changes within ±10% in time as compared to the core material comprising methylphenidate only. That is to say, the core material comprising the polymer material as well as methylphenidate exhibits identical or similar release pattern as compared to the core material comprising methylphenidate only. Specifically, the polymer material may be a water-soluble polymer such as hydroxypropyl methylcellulose (HPMC), polyvinylpyrrolidone (PVP), etc.

In an embodiment, the polymer material included in the core material may be one or more selected from a group consisting of an amino methacrylate copolymer, polyacrylate dispersion 30%, a methacrylic acid copolymer, carboxymethyl cellulose, ethyl cellulose, cellulose acetate, cellulose propionate, cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly(hexyl methacrylate), poly(isodecylmethyl methacrylate), poly(lauryl methacrylate), poly(phenyl methacrylate), poly(cetyl acrylate), poly(isopropyl acrylate), poly(isobutyl acrylate), poly(octadecyl acrylate), polyethylene terephthalate, hydroxyethyl cellulose, polydextrose, poly(acrylic acid), a carbomer, polyvinyl alcohol, polyvinylpyrrolidone, methyl cellulose, hydroxypropyl cellulose, agar, carrageenan, xanthan, hydroxypropyl methylcellulose, polyethylene glycol, shellac, polypropylene glycol, an ethyl acrylate-methyl methacrylate-chlorotrimethylammoniumethyl methacrylate copolymer, a methyl methacrylate-ethyl acrylate copolymer, and a methyl methacrylate-butyl methacrylate-dimethylaminoethyl methacrylate copolymer.

Polymer Coating Layer for Release Control

In an embodiment according to the present disclosure, the polymer coating layer for release control is coated on the core material and serves to control the release of the drug. The polymer coating layer for release control may be formed by coating on the core material using a general coater, a flow coater, a fluidized bed processor, a flow granulator, or the like. The polymer coating layer may comprise one or more polymers.

As used herein, the "average thickness" of the particle group refers to the average thickness of 10 particles of the polymer coating layer for release control randomly selected from each particle group. The average thickness is measured by observing the fracture surface of the particles using a scanning electron microscope (SEM). The release pattern of the prepared particles for release control may be tested for example by a release test.

In an embodiment of the present disclosure, the polymer material of the polymer coating layer for release control may be one or more selected from a group consisting of a water-insoluble polymer, a water-soluble polymer, an enteric polymer and a gastric polymer. Specifically, the polymer material may be one or more water-insoluble polymer material, or a combination of one or more water-insoluble polymer and one or more polymer material selected from a group consisting of a water-insoluble polymer, a water-soluble polymer, an enteric polymer and a gastric polymer. In an embodiment of the present disclosure, one or more water-insoluble polymer may be included to deliver the sustained-release drug. The combination of the polymer materials is used to adequately combine the polymers with specific properties depending on the desired release pattern of the drug or the formulation form.

In an embodiment, the water-insoluble polymer material may be one or more selected from a group consisting of a water-insoluble cellulose ether and a water-insoluble acrylic acid-based copolymers. For example, ethyl cellulose, an ethyl acrylate-methyl methacrylate-chlorotrimethylammoniumethyl methacrylate copolymer, a methyl methacrylate-ethyl acrylate copolymer (e.g., Eudragit® NE30D, Eudragit® NE40D or Eudragit® NM30D), polyvinyl acetate (e.g., Kollicoat® SR30D), or the like are included. The ethyl acrylate-methyl methacrylate-chlorotrimethylammoniumethyl methacrylate copolymer may include ammonio methacrylate units in an amount of 8.85-11.96% (e.g., Eudragit® RL) or 4.48-6.77% (e.g., Eudragit® RS).

In an embodiment, the water-soluble polymer material may be one or more selected from a group consisting of a water-soluble cellulose ether, a water-soluble polyvinyl derivative, and an alkylene oxide polymer. For example, methyl cellulose, hydroxypropyl cellulose, hydroxypropyl methylcellulose, polyvinylpyrrolidone, polyvinyl alcohol, polyethylene glycol, polypropylene glycol, or the like are included.

In an embodiment, the enteric polymer material may be one or more selected from a group consisting of an enteric cellulose derivative, an enteric acrylic acid-based copolymer, an enteric maleic acrylic acid-based copolymer, and an enteric polyvinyl derivative. For example, hydroxypropyl methylcellulose acetate succinate, hydroxypropylmethyl cellulose phthalate, hydroxymethyl ethyl cellulose phthalate, cellulose acetate phthalate, cellulose acetate succinate, cellulose acetate maleate, cellulose benzoate phthalate, cellulose propionate phthalate, methylcellulose phthalate, carboxymethyl ethyl cellulose, ethyl hydroxyethyl cellulose phthalate, a styrene-acrylic acid copolymer, a methyl acrylate-acrylic acid copolymer, a methyl acrylate-methacrylic acid copolymer, a butyl acrylate-styrene-acrylic acid copolymer, a methacrylic acid-methyl acrylate copolymer, a methacrylic acid-ethyl acrylate copolymer, a methyl acrylate-methacrylic acid-octyl acrylate copolymer, a vinyl acetate-maleic anhydride copolymer, an ethylene-maleic anhydride copolymer, a vinyl butyl ether-maleic anhydride copolymer, an acrylonitrile-methyl acrylate-maleic anhydride copolymer, a butyl acrylate-styrene-maleic anhydride copolymer; polyvinyl alcohol phthalate, polyvinyl acetal phthalate, polyvinyl butylate phthalate, polyvinyl acetate acetal phthalate, or the like are included.

In an embodiment, the gastric polymer may be one or more selected from a group consisting of a gastric polyvinyl derivative and a gastric acrylic acid-based copolymer. For example, polyvinyl acetal diethylamino acetate, a methyl methacrylate-butyl methacrylate-dimethylaminoethyl methacrylate copolymer (e.g., Eudragit E), or the like are included.

In an embodiment of the present disclosure, the polymer of the polymer coating layer for release control may be an ethyl acrylate-methyl methacrylate-chlorotrimethylammoniumethyl methacrylate copolymer (including ammonio methacrylate units in an amount of 8.85-11.96% or 4.48-6.77%), a methyl methacrylate-ethyl acrylate copolymer, ethyl cellulose (e.g., Eudragit® NE30D, Eudragit® NE40D or Eudragit® NM30D), polyvinyl acetate (e.g., Kollicoat® SR30D), or the like, more specifically, an ethyl acrylate-methyl methacrylate-chlorotrimethylammoniumethyl methacrylate copolymer (including ammonio methacrylate units in an amount of 4.48-6.77%).

When forming the polymer coating layer for release control, a variety of materials may be added for various supplementary purposes, such as coating efficiency, drug stability, appearance, color, protection, maintenance, binding, performance improvement, preparation process improvement, supplementary release control, or the like. The additive material may include a sugar, a sugar alcohol, a colorant, an aromatic, a sweetener, a surfactant, a lubricant, a stabilizer, an antioxidant, a foaming agent, paraffin, wax, an anti-foaming agent, a plasticizer, or the like. The selection and usage of the additive material and coating thereof on the core material may be easily accomplished by those skilled in the art and may be modified variously.

In an embodiment, the plasticizer included in the core material and the polymer coating layer for release control may be acetyl triethyl citrate, dibutyl phthalate, tributyl citrate, triethyl citrate, propylene glycol, triacetin, polyethylene glycol, diethyl phthalate, dibutyl sebacate, diethyl sebacate, cetyl alcohol, stearyl alcohol, cetostearyl alcohol, or the like, but is not limited thereto. Specifically, dibutyl phthalate, diethyl phthalate, dibutyl sebacate, diethyl sebacate, or the like may be used. The plasticizer may be included in an amount of 0-60 wt % based on the dry weight of the polymer.

In an embodiment, the lubricant included in the core material and the polymer coating layer for release control may be stearic acid, glyceryl behenate, glyceryl monostearate, magnesium stearate, calcium stearate, silicon dioxide, talc, magnesium silicate, or the like, but is not limited thereto. The lubricant may be included in an amount of 0.001-300 wt % based on the dry weight of the polymer. When the content of the lubricant is below 0.001 wt %, glidant or anti-tacking effect may be insufficient. And, when it exceeds 300 wt %, the addition of the lubricant may result in reduced efficiency.

The average diameter of the particles for release control is in the range from 30 to 3500 μm, specifically from 50 to 2000 μm, more specifically from 100 to 1500 μm. In another embodiment, when preparing an orally disintegrating tablet or a chewable tablet, particles having a diameter of 100 to 800 μm may be used in order to minimize foreign body sensation in the mouth, but without being particularly limited thereto.

In an embodiment, the particles for release control may further comprise one or more coating(s) selected from a sub-coating inside the polymer coating layer and an over-coating outside the polymer coating layer. The sub-coating or over-coating serves to confer or improve various supplementary purposes, such as stabilization or protection of the drug, drug-containing particles or final formulation, coloring, masking of bitter taste, etc., with little or no effect on the release control of the drug. The sub-coating or over-coating may comprise a sugar, a sugar alcohol, a polymer material, a colorant, an aromatic, a sweetener, a surfactant, a lubricant, a stabilizer, a foaming agent, paraffin, wax, a plasticizer, an antioxidant, or the like.

Particle Group for Release Control

Particle groups with identical polymer(s) included in the polymer coating layer but different average thickness of the coating layer may be obtained by varying the amount of the coating material. Since the change in the thickness of the polymer coating layer results in the change in the release pattern of the drug, the drug release pattern may be controlled with a combination of particle groups having different coating layer thicknesses. That is to say, after preparing particle groups with different average thicknesses and simulating drug release for various combinations of the particle groups, specific combinations of particular particle groups providing a desired drug release pattern can be obtained. The particular particle groups may be two, three, four or more particle groups.

In an embodiment of the present disclosure, the number of the particle groups for release control may be two or more, specifically two or three.

In an embodiment, when the number of the particle groups for release control is two, a first particle group may have an average coating layer thickness of 1 to 120 μm, and a second particle group may have an average coating layer thickness of 10 to 250 μm. The average coating layer thickness of each particle group may increase gradually. Specifically, the first particle group may have an average coating layer thickness of 2 to 80 μm, and the second particle group may have an average coating layer thickness of 10 to 120 μm. More specifically, the first particle group may have an average coating layer thickness of 2 to 60 μm, and the second particle group may have an average coating layer thickness of 20 to 100 μm. The difference of the average coating layer thickness of the first particle group and the second particle group may be 5 to 240 μm, specifically 10 to 100 μm.

In another embodiment, when the number of the particle groups for release control is three, a first particle group may have an average coating layer thickness of 1 to 120 μm, a second particle group may have an average coating layer thickness of 5 to 200 μm, and a third particle group may have an average coating layer thickness of 10 to 250 μm. The average coating layer thickness of each particle group may increase gradually. More specifically, when the number of the particle groups for release control is three, the first particle group may have an average coating layer thickness of 2 to 90 μm, the second particle group may have an average coating layer thickness of 5 to 120 μm, and the third particle group may have an average coating layer thickness of 10 to 150 μm. More specifically, when the number of the particle groups for release control is three, the first particle group may have an average coating layer thickness of 2 to 30 μm, the second particle group may have an average coating layer thickness of 30 to 60 μm, and the third particle group may have an average coating layer thickness of 45 to 90 μm.

The difference of the average coating layer thickness of the first particle group and the second particle group may be 5 to 190 μm, specifically 10 to 70 μm, and the difference of the average coating layer thickness of the second particle group and the third particle group may be 5 to 240 μm, specifically 10 to 80 μm.

In case the composition of the polymer included in each particle group is identical in terms of polymer type and its composition ratio, the coating solution may be prepared at once in large scale since the coating solution is identical. Further, various particle groups may be obtained from a single batch of production since the desired particle groups can be taken as the production is carried out. In another case, after a particle group having a smaller coating layer thickness is prepared, some of the particles may be used as a seed for the preparation of a particle group with a larger coating layer thickness. In this way, the production time can be decreased since the time required for coating of the second particle group decreases.

In another embodiment, the polymer coating layer for release control may comprise two or more layers. When the coating layer comprises two or more layers, the drug release pattern can be controlled more variously. When coating the particles into two or more layers, the polymer composition of each layer may be identical or different. For example, the polymer coating layer for release control may comprise 2 to 5 layers, and the polymer composition of each layer may be partly or completely different. In case the polymer coating layer comprises two or more layers, the average thickness of all or some of the layers may be different for each particle group.

In another embodiment, cores with different diameters may be used to prepare the particle groups for release control in order to prevent nonuniform mixing of the particle groups that may occur due to the large difference in the average diameter of the selected particle groups when combining them. For example, if the first particle group has a smaller average diameter as compared to the second and third particle group, a seed having a larger diameter may be used to prepare the first particle group as drug core, and then the polymer coating layer may be formed thereon. In this way, the nonuniform mixing of the particle groups may be avoided since the relative difference in the average diameter decreases.

In an embodiment, when the number of the particle groups for release control is three, the drug release pattern of each particle group tested according to the method 2(paddle method) of "36. release test method" of the Korean Pharmacopoeia, 8th edition (KP VIII) in 500 mL of water at 50 rpm exhibits:

the release of the drug included in the first particle group is 70 wt % or more within 1 hour, the release of the drug included in the second particle group is 30 wt % or less within 1 hour, and 70 wt % or more within 6 hours, and the release of the drug included in the third particle group is 30 wt % or less within 2 hours, and 70 wt % or more within 8 hours.

In addition to the thickness of the polymer coating layer, the weight proportion of the particle groups may result in a different release pattern. In an embodiment of the present disclosure, when the number of the particle groups for release control is three, the weight proportion of the first particle group: the second particle group: the third particle group may be 1:0.1-10:0.1-10, specifically 1:0.2-8:0.2-8, more specifically 1:0.5-6:1-8. Since the average coating layer thickness may be varied to obtain the desired release pattern, the weight proportion may also be varied accordingly.

The release pattern of the pharmaceutical composition with combination of particle groups tested according to the method 2(paddle method) of "36. release test method" of KP VIII in 500 mL of water at 50 rpm may exhibit:

(a) 5 to 50% of the total drug is released within 1 hour,
(b) 10 to 65% of the total drug is released within 2 hours,
(c) 20 to 80% of the total drug is released within 4 hours,
(d) 30 to 95% of the total drug is released within 6 hours, and
(e) 50% or more of the total drug is released within 8 hours.

Specifically, the release pattern of the pharmaceutical composition with combination of particle groups tested according to the method 2(paddle method) of "36. release test method" of KP VIII in 500 mL of water at 50 rpm may exhibit:

(a) 10 to 40% of the total drug is released within 1 hour,
(b) 15 to 50% of the total drug is released within 2 hours,
(c) 30 to 75% of the total drug is released within 4 hours,
(d) 50 to 90% of the total drug is released within 6 hours, and
(e) 70% or more of the total drug is released within 8 hours.

In this case, since some of the drug is released within 1 hour of medication, the medicinal effect can be attained early. Further, since the drug is released slowly for 8 hours, the medicinal effect can be sustained for about 12 hours with just one medication in the morning. This means that, if the patient takes the drug at around 8 a.m., the medicinal effect lasts until 8 p.m. Thus, the medicinal effect persists while the patient is awake with just one medication a day.

Formulation

The present disclosure further provides an oral formulation comprising the pharmaceutical composition for release control. The oral formulation may be prepared into various types without particular limitation. In an embodiment, the oral formulation may be a capsule, a general tablet, a double layered tablet, a chewable tablet, an orally disintegrating tablet, a dry syrup, a syrup, a jelly, a granule, and so forth. When preparing the oral formulation, an excipient, a disintegrant, a binder, a lubricant, a colorant, an aromatic, a sweetener, a surfactant, a stabilizer, a foaming agent, an antioxidant, or the like may be added as an additive.

In an embodiment, the pharmaceutical composition for release control may be prepared into a hard capsule by mixing with an additive such as a lubricant, an excipient, etc. and then filling in a hard capsule. Alternatively, the pharmaceutical composition for release control may be prepared into a general tablet by compressing together with an excipient, a disintegrant, a binder, a lubricant, a colorant, an aromatic, a sweetener, etc. The pharmaceutical composition for release control may also be prepared into a chewable tablet together with an excipient, a disintegrant, a binder, a lubricant, a colorant, an aromatic, a sweetener, or the like. Furthermore, the pharmaceutical composition for release control may be dispersed uniformly in syrup and methylphenidate of the pharmaceutical composition for release control may not be released in syrup during storage, it is applicable as a syrup.

As occasion demands, the pharmaceutical composition for release control may be prepared into an orally disintegrating tablet which is convenient for the patient to take. In this case, the patience convenience is maximized since the sustained-release, the orally disintegrating tablet can maintain the medicinal effect with just one medication a day and it can be taken without drinking water. For example, the orally disintegrating tablet may be prepared using known orally disintegrating tablet technologies such as WOWTAB®, Zydis®, OraSolv®, DuraSolv®, QuickSolv°, FlashTab®, AdvaTab®, Lyoc®, FlashDose®, Frosta®, etc.

Specifically, the pharmaceutical composition for release control may be a capsule or a tablet. Especially, it may be an orally disintegrating tablet. When preparing the tablet, it is desirable to appropriately adjust the compression pressure in order to avoid damage of the polymer coating layer of the pharmaceutical composition for release control. Alternatively, a substance that can act as a buffer may be included to avoid damage of the coating layer. In case of the orally disintegrating tablet, it is desirable to mask the bitter taste of methylphenidate since the tablet remains for a while in the mouth. The bitter taste may not be sufficiently masked only with the use of a sweetener or an aromatic. In this case, the particles coated on the core material may appropriately serve this purpose.

The various types of tablets may be prepared either by direct compression, i.e. by directly compressing the pharmaceutical composition for release control with an excipient without granulation, or by granulation, i.e. by preparing granules and then mixing the pharmaceutical composition with an excipient such as a lubricant and then performing compression. Alternatively, the composition for release control may be granulated after mixing with an excipient, and then compressed into tablet following a post-mixing process.

The formulation of the present disclosure may comprise 2 to 60 mg of methylphenidate per unit dose, and may be taken once to three times a day.

The examples and experiments will now be described. The following examples and experiments are for illustrative purposes only and not intended to limit the scope of this disclosure.

EXAMPLES

The properties of the formulations prepared in the following examples were analyzed as follows.

Release Test

Release test for the active ingredient of a particle, tablet, capsule, chewable tablet, and orally disintegrating tablet was performed according to the method 2(paddle method) of "36. release test method" of the Korean Pharmacopoeia, 8th edition (KP VIII). pH 1.2 buffer, pH 4.0 buffer, pH 6.8 buffer, or triple distilled water was used as the release solution.

High-performance liquid chromatography (HPLC) was employed for analysis. For analysis of methylphenidate, a 1:1:2 (v/v/v) mixture of 1.64 g of anhydrous sodium acetate dissolved in 1 L of water (balanced to pH 4.0 with acetic acid), acetonitrile and methanol was used as a mobile phase. USP L10 column (filled with cyano-silica gel, 250×4.6 mm) was used, and measurement was made for 8 minutes at a detection wavelength of 210 nm, with a flow rate of 1.5 mL/min and a sample volume of 50 μL. The drug peak was observed at a retention time of about 4.4 minutes.

Content Analysis

Content of the active ingredient included in a particle, tablet, capsule, chewable tablet, and orally disintegrating tablet was analyzed as follows. The particle, tablet, capsule, chewable tablet, or orally disintegrating tablet including the active ingredient was added to the mobile phase used in the release test. After mixing by shaking, the mixture was centrifuged. The supernatant was filtered and diluted to obtain a test solution, which was analyzed by HPLC. For analysis of methylphenidate content, the mobile phase used in the release test was used as a mobile phase. USP L10 column (filled with cyano-silica gel, 250×4.6 mm) was used, and measurement was made for 8 minutes at a detection wavelength of 210 nm, with a flow rate of 1.5 mL/min and a sample volume of 20 μL. The drug peak was observed at a retention time of about 4.4 minutes.

Hardens Measurement

Hardness of a tablet, chewable tablet, and orally disintegrating tablet was measured using an 8M hardness tester (8M, Dr. Schleuniger, Switzerland). Measurement was made for at least 6 samples and the average was taken.

Disintegration Test

Oral disintegration test of an orally disintegrating tablet was carried out on volunteers. The volunteers were randomly selected and asked to gargle. After putting the tablet on the tongue of the volunteer, the disintegration time was measured using a stopwatch. The volunteers were allowed to move the orally disintegrating tablet to the palate with his/her tongue or roll it without chewing. The time when the tablet was disintegrated so that it could be swallowed along with saliva was recorded.

Example 1

Preparation of Core Material Comprising Methylphenidate (Core 1)

Methylphenidate hydrochloride (850 g), talc (24 g) and hydroxypropyl methylcellulose (HPMC, 48.5 g) were dissolved in water (4800 g) to prepare a coating solution. Microcrystalline cellulose CP102 (106-212 μm, Celphere® Asahi Kasei, Japan, 425 g) was loaded in a GPCG-1 (Glatt, Germany) flow coater. While spraying the prepared coating solution by bottom spraying, coating was performed while maintaining the product temperature at 29-35° C. until the coating solution was exhausted. Then, after drying at 50° C., a core material (1330 g) comprising methylphenidate was obtained. The drug content measured by HPLC was about 65.4%. The obtained core material mostly passed through a 300 μm sieve. When analyzed by scanning electron microscopy (SEM), most of the particles had a diameter in the range from 180 to 300 μm.

A core material (1339 g) comprising methylphenidate was obtained by repeating the same procedure. The drug content measured by HPLC was about 65.9%. The obtained core material mostly passed through a 300 μm sieve. When analyzed by SEM, most of the particles had a diameter in the range from 180 to 300 μm.

Example 2

Preparation of Core Material Comprising Methylphenidate (core 2)

Methylphenidate hydrochloride (850 g), talc (24 g) and HPMC (48.5 g) were dissolved in water (4800 g) to prepare a coating solution. Microcrystalline cellulose CP203 (150-300 μm, Celphere® Asahi Kasei, Japan, 425 g) was loaded in a GPCG-1 flow coater. While spraying the prepared coating solution by bottom spraying, coating was performed while maintaining the product temperature at 29-35° C. until the coating solution was exhausted. Then, after drying at 50° C., a core material (1335 g) comprising methylphenidate was obtained. The drug content measured by HPLC was about 65.0%. The obtained core material mostly passed through a 425 μm sieve. When analyzed by SEM, most of the particles had a diameter in the range from 200 to 400 μm.

Example 3

Preparation of Core Material Comprising Methylphenidate (Core 3)

Methylphenidate hydrochloride (392 g) and Avicel® PH101 (208 g) were loaded in a GPCG-1 fluidized bed processor equipped with a rotor. Then, spherical particles were prepared by spraying water (500 g) while operating the rotor at 1400 rpm. When spherical particles with a size of 150 to 300 μm were prepared, the spraying was stopped and the particles were dried at 50° C. for 10 minutes. After stopping the rotation, the product was dried in a convection oven for 8 hours, and then sieved. Particles with a size of 150-300 μm (438 g) were obtained. The drug content measured by HPLC was about 64.9%.

Example 4

Preparation of Particles for Release Control A

Eudragit® RS 100 (Degussa, 65 g) was dissolved in a mixture solvent of ethanol (468 g) and water (155 g) and talc (19.6 g) was added to prepare a coating solution. The core material prepared in Example 1 (core 1, 500 g) was loaded in a flow coater. While spraying the prepared coating solution by bottom spraying, coating was performed while maintaining the product temperature at 26-32° C. until the coating solution was exhausted. Then, after drying, particles for release control (572 g) were obtained. The drug content measured by HPLC was about 54.5%.

The polymer for release control was coated with an amount of about 13% based on the core material comprising methylphenidate. When the fracture surface was observed by SEM, the thickness of the polymer coating layer was 9.6±5.0 μm.

Example 5

Preparation of Particles for Release Control B

Eudragit® RS 100 (Degussa, 40 g) was dissolved in a mixture solvent of ethanol (288 g) and water (95 g) and talc (12 g) was added to prepare a coating solution. The core material prepared in Example 2 (core 2, 500 g) was loaded in a flow coater. While spraying the prepared coating solution by bottom spraying, coating was performed while maintaining the product temperature at 26-32° C. until the coating solution was exhausted. Then, after drying, particles for release control (543 g) were obtained. The drug content measured by HPLC was about 58.4%.

The polymer for release control was coated with an amount of about 8% based on the core material. When the fracture surface was observed by SEM, the thickness of the polymer coating layer was 8.4±5.2 μm.

Example 6

Preparation of Particles for Release Control C

Eudragit® RS 100 (Degussa, 575 g) was dissolved in a mixture solvent of ethanol (4140 g) and water (1376 g) and talc (173 g) was added to prepare a coating solution. The core material prepared in Example 1 (core 1, 500 g) was loaded in a flow coater. While spraying the prepared coating solution by bottom spraying, coating was performed while maintaining the product temperature at 26-32° C. until the coating solution was exhausted. Then, after drying, particles for release control (1210 g) were obtained. The drug content measured by HPLC was about 26.2%.

The polymer for release control was coated with an amount of about 115% based on the core material comprising methylphenidate. When the fracture surface was observed by SEM, the thickness of the polymer coating layer was 55.8±6.8 μm.

Example 7

Preparation of Particles for Release Control D

Eudragit® RS 100 (Degussa, 1250 g) was dissolved in a mixture solvent of ethanol (9000 g) and water (2990 g) and talc (377 g) was added to prepare a coating solution. The core material prepared in Example 1 (500 g) was loaded in a flow coater. While spraying the prepared coating solution by bottom spraying, coating was performed while maintaining the product temperature at 26-32° C. until the coating solution was exhausted. Then, after drying, particles for release control (2080 g) were obtained. The drug content measured by HPLC was about 15.0%.

The polymer for release control was coated with an amount of about 250% based on the core material comprising methylphenidate. When the fracture surface was observed by SEM, the thickness of the polymer coating layer was 79.7±7.4 μm.

Example 8

Preparation of Particles for Release Control E

Eudragit® RS 100 (Degussa, 1500 g) was dissolved in a mixture solvent of ethanol (10800 g) and water (3600 g) and talc (450 g) was added to prepare a coating solution. The core material comprising methylphenidate prepared in Example 1 (500 g) was loaded in a flow coater. While spraying the prepared coating solution by bottom spraying, coating was performed while maintaining the product temperature at 26-32° C. until the coating solution was exhausted. Then, after drying, particles for release control (2370 g) were obtained. The drug content measured by HPLC was about 13.5%.

The polymer for release control was coated with an amount of about 300% based on the core material comprising methylphenidate. When the fracture surface was observed by SEM, the thickness of the polymer coating layer was 82.3±8.6 μm.

The particles for release control prepared in Examples 4 to 8 are summarized in Table 1.

TABLE 1

|  | Particles A | Particles B | Particles C | Particles D | Particles E |
| --- | --- | --- | --- | --- | --- |
| Seed | Core 1, 500 g | Core 2, 500 g | Core 1, 500 g | Core 1, 500 g | Core 1, 500 g |
| Eudragit ® RS 100 | 65 g | 40 g | 575 g | 1250 g | 1500 g |
| Ethanol | 468 g | 288 g | 4140 g | 9000 g | 10800 g |
| Water | 155 g | 95 g | 1376 g | 2990 g | 3600 g |
| Talc | 19.6 g | 12 g | 173 g | 377 g | 450 g |
| Thickness (μm) | 9.6 ± 5.0 | 8.4 ± 5.2 | 55.8 ± 6.8 | 79.7 ± 7.4 | 82.3 ± 8.6 |

Example 9

Release Test of Particles for Release Control in Water

Release pattern of the particles prepared in Examples 4 to 8 in water was tested according to the aforesaid release test method. Particles A were precisely weighed to prepare 6 samples (49.5 mg) and tested in water (500 mL) according to the paddle method at 50 rpm for 12 hours. The release curve was obtained by averaging the HPLC analysis result. Particles B, C, D and E were precisely weighed in amounts of 46.2 mg, 103 mg, 180 mg and 200 mg, respectively, and tested in the same manner as above. The result is given in Table 2.

TABLE 2

| | Drug release (%) | | | | |
| --- | --- | --- | --- | --- | --- |
| Release time | Particles A | Particles B | Particles C | Particles D | Particles E |
| 1 hour | 96.6 | 97.3 | 4.4 | 0 | 0 |
| 2 hours | 100.3 | 99.4 | 17.1 | 0.7 | 0.9 |
| 4 hours | 99.9 | 99.1 | 61.0 | 3.8 | 1.9 |
| 6 hours | 99.7 | 100 | 99.8 | 20.4 | 14.6 |
| 8 hours | 99.4 | 99.2 | 99.4 | 87.5 | 72.1 |

Example 10

Combination 1 of Particles

Particle groups A, C and D prepared in Examples 4 to 8 were taken 6 times in amounts of 10.9 mg, 39.2 mg and 72 mg, respectively, and tested in water (500 mL) according to the paddle method at 50 rpm for 12 hours. The result of HPLC analysis is given in Table 3. The same result was obtained when particle group B (10.2 mg) was used instead of particle group A.

Example 11

Combination 2 of Particles

Particle groups A, C and E prepared in Examples 4 to 8 were taken 6 times in amounts of 17.3 mg, 36.1 mg and 60 mg, respectively, and tested in water (500 mL) according to the paddle method at 50 rpm for 12 hours. The result of HPLC analysis is given in Table 3. The same result was obtained when particle group B (16.1 mg) was used instead of particle group A.

TABLE 3

| Release time | Drug release (%) | |
|---|---|---|
| | Combination 1 of particles | Combination 2 of particles |
| 1 hour | 22.9 | 35.6 |
| 2 hours | 28.8 | 41.4 |
| 4 hours | 46.7 | 56.9 |
| 6 hours | 68.0 | 74.2 |
| 8 hours | 94.4 | 90.8 |

Combination 1 of particles exhibited initial medicinal effect, with about 20% of drug released within 1 hour after medication. Furthermore, it exhibited sustained medicinal effect lasting about 12 hours with just one medication in the morning, since the drug was slowly released for 8 hours. This means that, if the patient takes the drug at around 8 a.m., the medicinal effect lasts until 8 p.m. Thus, the medicinal effect persists while the patient is awake with just one medication a day.

Combination 2 of particles exhibited initial medicinal effect, with about 35% of drug released within 1 hour after medication. Furthermore, it exhibited sustained medicinal effect lasting about 12 hours with just one medication in the morning, since the drug was slowly released for 8 hours.

Example 12

Preparation of Particles for Release Control F, G and H, Combination of Particles Particles for release control F, G and H comprising dibutyl sebacate as a plasticizer were prepared as described in Table 4. Except for the addition of the plasticizer, the procedure was the same as that described in Examples 4 to 8. Thickness of the polymer coating layer measured by SEM and drug content measured by HPLC are also given in Table 4.

TABLE 4

| | Particles F | Particles G | Particles H |
|---|---|---|---|
| Seed | Core 1, 500 g | Core 1, 500 g | Core 1, 500 g |
| Eudragit ® RS 100 | 60.5 g | 402.9 g | 741.7 g |
| Dibutyl sebacate (DBS) | 3.025 g | 19.83 g | 37.1 g |
| Ethanol | 435 g | 2900 g | 5340 g |
| Water | 145 g | 967 g | 1780 g |
| Talc | 18.2 g | 121.1 g | 222.2 g |
| Thickness (μm) | 4.8 ± 1.1 | 43.6 ± 3.1 | 66.7 ± 5.5 |
| Drug content | 54.2% | 30.2% | 21.0% |

The prepared particle groups F, G and H were taken 6 times in amounts of 11.5 mg, 24.1 mg and 64.3 mg, respectively, and tested in water (500 mL) according to the paddle method at 50 rpm for 12 hours. The result of HPLC analysis is given in Table 5.

TABLE 5

| Release time | Drug release (%) |
|---|---|
| 1 hour | 23.4 |
| 2 hours | 26.5 |
| 4 hours | 50.5 |
| 6 hours | 77.3 |
| 8 hours | 91.6 |

They exhibited initial medicinal effect, with about 23.4% of drug released within 1 hour after medication. Furthermore, it exhibited sustained medicinal effect lasting about 12 hours with just one medication in the morning, since the drug was slowly released for 8 hours. This means that, if the patient takes the drug at around 8 a.m., the medicinal effect lasts until 8 p.m. Thus, the medicinal effect persists while the patient is awake with just one medication a day.

Example 13

Orally Disintegrating Tablet

Mannogem EZ (spray dried mannitol, SPI, 190 g) was mixed with Advantose FS 95 (spray dried fructose, SPI, 10 g) and granulated using a 50% sucrose solution (ethanol:water=4:6, 40 g). The granulated particles passed through a 600 μm sieve and dried in an oven at 50° C. The prepared granule (118 g) was mixed with particles A, C and D (3.1 g, 11.3 g and 20.6 g, respectively, 35 g in total) prepared in Examples 4 to 8. After further mixing with a disintegrant (Explotab, 4.8 g) and a lubricant (2.4 g), the mixture was compressed into a 561 mg orally disintegrating tablet.

Hardness measurement and disintegration test were performed as described above. The orally disintegrating tablet had a hardness of 4.9 Kp and was disintegrated in the mouth in 28 seconds.

A similar result was obtained when particle group B (2.9 g) was used instead of particle group A. The orally disintegrating tablet had a hardness of 4.6 Kp and was disintegrated in the mouth in 30 seconds. But, the mixing time could be decreased because of good particle miscibility.

The invention claimed is:
1. A pharmaceutical composition for release control of methylphenidate comprising:
 a plurality of particles comprising a core material containing methylphenidate and a polymer coating layer formed on the core material, wherein the plurality of particles are identical in terms of the composition of the polymer in the polymer coating layer, but are divided into two or more particle groups based on the average thickness of the polymer coating layer, and wherein the particle groups comprise a first particle group having an average coating layer thickness of 1 to 30 μm, and a second particle group having an average coating layer thickness of 45 to 250 μm.

2. The pharmaceutical composition according to claim 1, wherein the polymer coating layer comprises a single layer or two or more layers.

3. The pharmaceutical composition according to claim 2, wherein, in the polymer coating layer comprising two or more layers, each layer is identical or different in terms of the composition of the polymer.

4. The pharmaceutical composition according to claim 1, wherein the particles further comprise a coating selected from a sub-coating inside the polymer coating layer and an over-coating outside the polymer coating layer.

5. The pharmaceutical composition according to claim 1, wherein the polymer of the polymer coating layer is one or more selected from a group consisting of a water-insoluble polymer, a water-soluble polymer, an enteric polymer, and a gastric polymer.

6. The pharmaceutical composition according to claim 1, wherein the particles have an average diameter of 30 to 3500 μm.

7. The pharmaceutical composition according to a claim 1, wherein the particle groups further comprise a third particle group.

8. The pharmaceutical composition according to claim 1 7, wherein the first particle group has an average coating layer thickness of 2 to 30 μm, and the second particle group has an average coating layer thickness of 45 to 90 μm.

9. The pharmaceutical composition according to claim 7, wherein the weight ratio of the first particle group:the second particle group:the third particle group is 1:0.1-10:0.1-10.

10. The pharmaceutical composition according to claim 1, wherein the release profile of the pharmaceutical composition tested according to the method 2(paddle method) of "36. release test method" of the Korean Pharmacopoeia, 8th edition (KP VIII) in 500 mL of water at 50 rpm exhibits:

5 to 50% of the total drug is released within 1 hour,
10 to 65% of the total drug is released within 2 hours,
20 to 80% of the total drug is released within 4 hours,
30 to 95% of the total drug is released within 6 hours, and
50% or more of the total drug is released within 8 hours.

11. The pharmaceutical composition according to claim 10, wherein the release profile of the pharmaceutical composition tested according to the method 2 (paddle method) of "36. release test method" of KP VIII in 500 mL of water at 50 rpm exhibits:

10 to 40% of the total drug is released within 1 hour,
15 to 50% of the total drug is released within 2 hours,
30 to 75% of the total drug is released within 4 hours,
50 to 90% of the total drug is released within 6 hours, and
70% or more of the total drug is released within 8 hours.

12. The pharmaceutical composition according to claim 1, wherein the core material and the polymer coating layer further comprise one or more selected from a group consisting of a sugar, a sugar alcohol, a polymer material, a colorant, an aromatic, a sweetener, a surfactant, a lubricant, a stabilizer, an antioxidant, a foaming agent, paraffin, wax, and a plasticizer.

13. The pharmaceutical composition according to claim 12, wherein the plasticizer is one or more selected from a group consisting of acetyl triethyl citrate, dibutyl phthalate, tributyl citrate, triethyl citrate, acetyl triethyl citrate, propylene glycol, triacetin, polyethylene glycol, diethyl phthalate, dibutyl sebacate, diethyl sebacate, cetyl alcohol, stearyl alcohol, and cetostearyl alcohol.

14. The pharmaceutical composition according to claim 1, wherein the pharmaceutical composition is an oral formulation.

15. The pharmaceutical composition according to claim 14, wherein the oral formulation is an orally disintegrating tablet, a chewable tablet, a capsule, a general tablet, a granule, or a syrup.

16. The pharmaceutical composition according to claim 7, wherein the difference between the average coating layer thickness of the second particle group and the third particle group is 10 to 80 μm.

17. The pharmaceutical composition according to claim 1, wherein the polymer of the polymer coating layer is water-insoluble ethyl acrylate-methyl methacrylate-chlorotrimethylammoniumethyl methacrylate copolymer.

* * * * *